United States Patent
Kurtzberg et al.

(10) Patent No.: US 11,278,575 B2
(45) Date of Patent: Mar. 22, 2022

(54) COMPOSITIONS AND METHODS FOR THE TREATMENT OF DEMYELINATING CONDITIONS

(71) Applicant: Duke University, Durham, NC (US)

(72) Inventors: Joanne Kurtzberg, Durham, NC (US); Andrew E. Balber, Durham, NC (US); Arjun Saha, Durham, NC (US); Pamela Noldner, Durham, NC (US); Paula Scotland, Durham, NC (US)

(73) Assignee: Duke University, Durham, NC (US)

( * ) Notice: Subject to any disclaimer, the term of this patent is extended or adjusted under 35 U.S.C. 154(b) by 341 days.

(21) Appl. No.: 16/510,395

(22) Filed: Jul. 12, 2019

(65) Prior Publication Data

US 2020/0038456 A1 Feb. 6, 2020

Related U.S. Application Data (60) Provisional application No. 62/697,270, filed on Jul. 12, 2018.

(51) Int. Cl.
| | | |
|---|---|---|
| *A61K 35/51* | (2015.01) | |
| *A61K 9/00* | (2006.01) | |
| *A61K 31/573* | (2006.01) | |

(52) U.S. Cl.
CPC ............ *A61K 35/51* (2013.01); *A61K 9/0019* (2013.01); *A61K 31/573* (2013.01)

(58) Field of Classification Search
CPC ...................................................... A61K 35/51
See application file for complete search history.

(56) References Cited

U.S. PATENT DOCUMENTS

| | | |
|---|---|---|
| 2006/0159666 A1 | 7/2006 | Willing et al. |
| 2015/0216899 A1 | 8/2015 | Pusic et al. |
| 2016/0060597 A1 | 3/2016 | Hornyak et al. |
| 2017/0296527 A1 | 10/2017 | Kottayil et al. |
| 2019/0343882 A1 | 11/2019 | Kurtzberg et al. |
| 2021/0275583 A1 | 9/2021 | Kurtzberg et al. |

FOREIGN PATENT DOCUMENTS

WO 2018132728 7/2018

OTHER PUBLICATIONS

Arnett HA, et al. TNF alpha promotes proliferation of oligodendrocyte progenitors and remyelination. Nat Neurosci. 4 (11):1116-1122 (2001).

Kurtzberg J, et al. Preclinical characterization of DUOC-01, a cell therapy product derived from banked umbilical cord blood for use as an adjuvant to umbilical cord blood transplantation for treatment of inherited metabolic diseases. Cytotherapy; 17(6):803-815 (2015).

(Continued)

*Primary Examiner* — Rosanne Kosson
(74) *Attorney, Agent, or Firm* — Polsinelli PC; Michelle L. McMullen (57) ABSTRACT

The present disclosure provides compositions and methods for treating demyelinating conditions. More particularly, the present disclosure relates to compositions including DUOC-01 cell product and an anti-inflammatory agent; methods for preparing such compositions; and methods of using such compositions in combination or in conjunction with each other for treatment of treating demyelinating conditions.

18 Claims, 3 Drawing Sheets

Cuprizone (56) References Cited

OTHER PUBLICATIONS

Larsen PH, et al. Matrix metalloproteinase-9 facilitates remyelination in part by processing the inhibitory NG2 proteoglycan. J Neurosci. 23(35):11127-11135 (2003).
Saha A, et al. A cord blood monocyte-derived cell therapy product accelerates brain remyelination. JCI Insight. 1 (13):e86667 (2016).
Sanberg PR, et al. Monocyte transplantation for neural and cardiovascular ischemia repair. J Cell Mol Med. 14 (3):553-563 (2010).
Scotland P, et al. Gene products promoting remyelination are up-regulated in a cell therapy product manufactured from banked human cord blood. Cytotherapy. 19(6):771-782 (2017).
Shechter R, et al. Harnessing monocyte-derived macrophages to control central nervous system pathologies: no longer 'if' but 'how'. J Pathol. 229(2):332-346 (2013).
Sun JM, et al. Cord blood for brain injury. Cytotherapy. 17(6):775-785 (2015).
Womble TA, et al. Monocytes are essential for the neuroprotective effect of human cord blood cells following middle cerebral artery occlusion in rat. Mol Cell Neurosci. 59:76-84 (2014).
Yang et al. Adult neural stem cells expressing IL-10 confer potent immunomodulation and remyelination in experimental autoimmune encephalitis. J Clin Invest. 119(12):3678-3691(2009).
Bacia et al, "K+ Channel Blockade Impairs Remyelination in the Cuprizone Model," 2004, GLIA 48:156-165.
Baker et al., Critical appraisal of animal models of multiple sclerosis, 2011, Multiple Sclerosis Journal 17(6):647-657 2011).
Saha et al., "Cord blood derived cell therapy product, DUOC-01, accelerates remyelination in a murine model of cuprizone induced demyelination", Cytotherapy, Poster Abstract, 21st ISCT Annual Meeting, vol. 17, No. 6, Supplement, p. S55, Jun. 1, 2015.
Saha et al., "DUOC-01, a cord blood derived cell therapy product, ameliorates experimental autoimmune encephalomyelitis, a murine model for multiple sclerosis," Cytotherapy 22( 2020), pp. S31-S32.
Saha et al., "Duoc-01, a Cord Blood Derived Cell Therapy Product, Ameliorates Experimental Autoimmune Encephalomyelitis," Abstracts/Biol Blood Marrow Transplant 25 (2019), pp. S165-S166.
Saha et al., "Human Umbilical Cord Blood Derived Cell Therapy Product, DUOC-01, Ameliorates Experimental Autoimmune Encephalomyelitis, A Mouse Model For Multiple Sclerosis," Cytotherapy, Poster Abstract, vol. 21, No. 5, Supplement, p. S55, May 1, 2019.
Saha et al., "Human Umbilical Cord Blood-Derived Cell Therapy Product, DUOC-01, Ameliorates Experimental Autoimmune Encephalomyelitis, a Mouse Model for Multiple Sclerosis," Stem Cells Translational Medicine, Sep. 2019, 1 page.
Saha et al., Hydrocortisone-Treated DUOC-01, a Cord Blood-Derived Cell Therapy Product, Ameliorates Experimental Autoimmune Encephalomyelitis, Stem Cells Translational Medicine, Sep. 2020, 1 page.
Sheykhansari et al., "Redox metals homeostasis in multiple sclerosis and amyotrophic lateral sclerosis: A review," 2018, Cell Death and Disease (2018)9:348, 16 pages.
Sun et al., "Augumentation of Allogenic Cord Blood (CB) Transplantation for Inherited Metabolic Diseases with CB-Derived Intrathecal Cellular Therapy, Duoc-01," Abstracts / Biol Blood Marrow Transplant 23 (2017), p. S100.

COMPOSITIONS AND METHODS FOR THE TREATMENT OF DEMYELINATING CONDITIONS

CROSS REFERENCE TO RELATED APPLICATIONS

This application claims priority to U.S. Provisional Patent Application Serial Number 62/697,270, filed Jul. 12, 2018, the contents of which are hereby incorporated by reference in their entirety.

BACKGROUND OF THE INVENTION

Field of the Invention

The present disclosure provides compositions and methods for treating demyelinating conditions. More particularly, the present disclosure relates to compositions comprising a DUOC-01 cell product and an anti-inflammatory agent; methods for preparing such compositions; and methods of using such compositions for treating demyelinating conditions. The present invention also includes methods for treating demyelinating conditions using a DUOC-01 cell product and an anti-inflammatory agent administered in combination or conjunction with each other.

Description of the Related Art

Microglia play critical but incompletely understood roles in propagation and resolution of central nervous system (CNS) injuries. These cells modulate neuroinflammation, produce factors that regulate activities of astrocytes, oligodendrocytes, and neurons, and clear debris to provide an environment for oligodendrocytes to begin to remyelinate neurons. In mice, microglia arise from a unique pool of replicating precursors in the brain that is originally derived from the extraembryonic yolk sac early in fetal development. Bone marrow-derived, circulating blood monocytes constitute another potential source of infiltrating phagocytic cells that can exacerbate or ameliorate CNS damage. Although a pathway for circulation of monocytes between lymph and brain parenchyma has recently been described, large numbers of circulating monocytes do not enter the uninjured, adult mouse brain but may infiltrate the CNS following insult such as brain irradiation, chemotherapy or injury, demyelinating conditions, or chronic stress. In some models, these infiltrating blood monocytes may activate inflammation and participate in demyelinating events. In others, blood monocytes may facilitate remyelination.

Limited information is available concerning the role of human blood monocytes in the dynamics of repair of brain injury. Circulating human monocytes include subpopulations that differ in their ability to migrate to tissues, proliferate, and form inflammatory or reparative macrophages at sites of injury. Based on experiments in rodents, several groups have proposed that cell products composed of human monocytes could be considered as candidates for the treatment of injury-induced CNS demyelination (Shechter R, Schwartz M. *J Pathol.* 2013; 229(2):332-346; Sanberg P R, et al. *J Cell Mol Med.* 2010; 14(3):553-563). CD14+ monocytes present in human umbilical cord blood (CB) are among these candidates. CB mononuclear cells are protective in several in vitro culture and animal models of CNS injury (Sun J M, Kurtzberg J. *Cytotherapy.* 2015; 17(6):775-785), and CB CD14+ cells are essential for the protective ability of intravenously injected CB mononuclear cells in the rat middle cerebral artery occlusion model of stroke (Womble T A, et al. *Mol Cell Neurosci.* 2014; 59:76-84).

The inventors have developed DUOC-01, a cell therapy product composed of cells with characteristics of macrophages and microglia that is intended for use in the treatment of demyelinating CNS diseases. DUOC-01 is manufactured by culturing banked cryopreserved and thawed CB-derived mononuclear cells (MNCs) in adherent cell culture over 21 days. The motile, phagocytic cells in DUOC-01 express CD45, CD11b, CD14, CD16, CD206, ionized calcium binding adaptor molecule 1 (Iba1), HLA-DR, and iNOS, secrete IL-10 and IL-6, and upregulate secretion of anti-inflammatory cytokines both constitutively and in response to TNF-α and IFN-γ (Kurtzberg J, et al. *Cytotherapy.* 2015; 17(6):803-815). DUOC-01 cells derived from genetically normal umbilical cord blood donors also secrete a battery of lysosomal hydrolases that are missing in children with leukodystrophies. DUOC-01, administered intrathecally 1-2 months after an unrelated donor umbilical cord blood transplant, provides cross-correcting normal enzyme to slow neurodegeneration before definitive engraftment by wild-type enzyme-producing cells from the systemic CB transplant.

The inventors have further combined DUOC-01 with hydrocortisone (HC), an anti-inflammatory agent, to improve the DUOC-01 for use in the treatment of demyelinating CNS diseases.

It has been currently determined that the use of hydrocortisone and DUOC-01 cells in combination or in conjunction with each other has the potential for therapeutic use in demyelinating conditions.

SUMMARY OF THE INVENTION

One aspect of the present invention provides a pharmaceutical composition comprising a DUOC-01 cell product and an anti-inflammatory agent in a pharmaceutically acceptable carrier. In some embodiments of the present invention, the anti-inflammatory agent improves the viability of the DUOC-01 cell product.

In some embodiments of the present invention, the anti-inflammatory agent is cortisone, hydrocortisone, triamcinolone, dexamethasone, or beclomethasone. In other embodiments of the present invention, the anti-inflammatory agent is hydrocortisone ("HC").

In some embodiments of the present invention, the DUOC-01 cell product comprises an amount of about $1 \times 10^4$ to about $1 \times 10^8$ cells.

Another aspect of the present invention provides a method of treating a demyelinating condition in a subject, the method comprising: administering to the subject in need thereof a therapeutically effective amount of a DUOC-01 cell product and an anti-inflammatory agent in a pharmaceutically acceptable carrier.

In some embodiments of the present invention, the DUOC-01 cell product comprises cells derived from cord blood mononuclear cells, wherein such cells express one or more of CD45, CD11b, CD14, CD16, CD206, CD163, Iba1, HLA-DR, TREM 2, and iNOS macrophage or microglia markers.

In some embodiments of the present invention, the demyelinating condition is leukodystrophies. In other embodiments of the present invention, the demyelinating condition is Krabbe disease, metachromatic leukodystrophy, Pelizaeus-Merzbacher disease, adrenoleukodystrophy (ALD), Tay Sachs disease, Hunter Syndrome, Sanfilippo Syndrome, Type A, or Batten disease. In yet other embodiments of the present invention, the demyelinating condition is multiple sclerosis. In yet other embodiments of the present invention, the demyelinating condition is spinal cord injury. In yet other embodiments of the present invention, the demyelinating condition is peripheral nerve damage. In yet other embodiments of the present invention, the demyelinating condition is Parkinson's disease, amyotrophic lateral sclerosis (ALS), or Alzheimer's disease.

In some embodiments of the present invention, the composition is administered via local tissue injection or intrathecally. In other embodiments of the present invention, the composition is administered in a single dose or in multiple doses.

In some embodiments of the present invention, the amount of composition administered is sufficient to provide the DUOC-01 cell product in an amount of about $1\times10^5$ to about $1\times10^7$ cells or about $1\times10^8$ to about $5\times10^6$ cells.

Another aspect of the present invention provides a kit comprising: a composition comprising a DUOC-01 cell product and an anti-inflammatory agent in a pharmaceutically acceptable carrier, and a label or instructions for administration of the composition to treat a demyelinating condition. The some embodiments, the demyelinating condition is multiple sclerosis, leukodystrophies, peripheral nerve disease, or spinal cord injury. In some embodiments, the anti-inflammatory agent is cortisone, hydrocortisone, triamcinolone, dexamethasone, or beclomethasone.

In another aspect, the present invention provides a method of treating demyelinating conditions through the use of a DUOC-01 cell product and an anti-inflammatory agent in conjunction with each other.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

DETAILED DESCRIPTION OF THE INVENTION

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Ranges can be expressed herein as from "about" one particular value, and/or to "about" another particular value. As used herein, the term "about" in association with a numerical value means that the numerical value can vary plus or minus by 5% or less of the numerical value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

As used herein, the term "contacting" includes the physical contact of at least one substance to another substance.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is at for, or suffering from, multiple sclerosis.

As used herein, the term "disease" refers to any condition that is abnormal, such as a disorder or a structure or function that affects part or all of a subject.

As used herein, the term "multiple sclerosis" refers to a neurological disorder that involves the degradation and/or destruction and/or deterioration of the myelin sheath.

As used herein, the term "demyelinating condition" refers to any condition that result in damage to the protective covering (myelin sheath) that surrounds nerve fibers in the brain, optic nerves, and spinal cord. Demyelinating conditions include, but are not limited to, leukodystrophies, multiple sclerosis, spinal cord injury, peripheral nerve damage, Parkinson's disease, amyotrophic lateral sclerosis (ALS), and Alzheimer's disease As used herein, the term "leukodystrophies" refers to a group of rare, metabolic, genetic diseases that affect the brain, spinal cord, and the peripheral nerves. Each type of leukodystrophy is caused by a specific gene abnormality that leads to abnormal development or destruction of the myelin sheath of the brain. Leukodystrophies, including but not limited to, Krabbe disease, metachromatic leukodystrophy, Pelizaeus-Merzbacher disease, adrenoleukodystrophy (ALD), Tay Sachs disease, Hunter Syndrome, Sanfilippo Syndrome, Type A, or Batten disease.

As used herein, the term "in conjunction with" refers to the use of two or more independent therapeutic agents to treat the same condition. The therapeutic agents may be used concurrently, i.e. at the same time, or one therapeutic agent may be administered prior to or after another therapeutic agent.

In view of the present disclosure, the methods and compositions described herein can be configured by the person of ordinary skill in the art to meet the desired need. In general, the disclosed materials, methods, and apparati provide improvements in treatment of demyelinating conditions. The inventors have found that HC did not decrease viability or alter the phenotype of DUOC-01 cells in vitro; in fact, HC improved the viability DUOC-01 cells over time. The inventors also found that HC did not change the expression level of surface markers used for standard characterization of DUOC-01 cells. The inventors further found that DUOC-01 cells exposed to HC promoted remyelination to the same extent as standard DUOC-01 cells.

Thus, one aspect of the disclosure provides methods for treating demyelinating conditions, such as leukodystrophies, multiple sclerosis, or spinal cord injury. Such methods include administering to the subject in need thereof a therapeutically effective amount of a composition comprising a DUOC-01 cell product and an anti-inflammatory agent in a pharmaceutically acceptable carrier.

In certain embodiments of the disclosure, the methods are for treating multiple sclerosis in a subject. In certain embodiments of the disclosure, the methods are for treating leukodystrophies in a subject. In certain embodiments of the disclosure, the methods are for treating spinal cord injury in a subject.

As noted above, the compositions useful in the methods of the disclosure include a DUOC-01 cell product. These cells were described by Kurtzberg J, et al. (*Cytotherapy.* 2015; 17(6):803-815), Saha A, et al. (*JCI Insight.* 2016; 1(13):e86667), and Scotland P (*Cytotherapy.* 2017; 19(6): 771-782), all incorporated by reference in their entirety. As understood by those in the art, the DUOC-01 cell product includes cells derived from cord blood mononuclear cells. In certain embodiments, such cells express one or more (e.g., one, two, three, four, or more) of CD45, CD11b, CD14, CD16, CD206, CD163, Iba1, HLA-DR, TREM 2, and iNOS macrophage or microglia markers. In certain embodiments, at least 50% of the cell population, e.g., at least 60%, or at least 70%, or at least 80%, or at least 85%, or even at least 90% of the cell population, expresses one or more (e.g., one, two, three, four, or more) of CD45, CD11 b, CD14, CD16, CD206, CD163, Iba1, HLA-DR, and iNOS macrophage or microglia markers.

Several of the proteins that are expressed by DUOC-01 cells are known to regulate the number or activity of oligodendrocyte progenitor cells (OPCs). PDGFs regulate the OPC numbers in the adult CNS and their activity following CNS demyelination, and PDGFA transcript expression was upregulated 32-fold in the DUOC-01 compared with CB CD14$^+$ monocytes. SCF has been implicated in the maintenance, migration, and survival of the OPC population, and its transcript was expressed at a 26-fold higher level in DUOC-01 cells than in CB CD14$^+$ cells.

TREM2 is another molecule expressed by DUOC-01 cells that plays an important role in remyelination. CD14$^+$ monocytes do not express TREM2 transcripts or protein. This surface receptor senses lipid debris and regulates signaling by glial cells that modulate myelination. It also functions in clearance of cellular and myelin debris, an important early step for recovery and remyelination following CNS injury. DUOC-01 cells are highly phagocytic and could play a significant role in myelin clearance and intercellular signaling through the TREM2 receptor.

DUOC-01 cell product of the disclosure expresses many other proteins that could participate more indirectly in promoting remyelination and in resolving cellular accumulation in the CC. Cytokine-activated microglia can stimulate the differentiation of oligodendrocytes from neural progenitor cells. While oligodendrocytes affect the remyelination of nerve fibers, other cell types are important for this repair process. Astrocytes provide trophic factors for oligodendrocytes and also for microglia. Microglia also provide trophic factors and remove myelin debris that inhibit remyelination by oligodendrocytes. It was previously reported that DUOC-01 cells secrete IL-10 and TNF-α in culture (Kurtzberg J, et al. *Cytotherapy.* 2015; 17(6):803-815). Yang et al. have demonstrated that neuronal stem cells producing IL-10 not only effectively suppress CNS inflammation but also promote remyelination and neuron/oligodendrocyte repopulation in a mouse model of experimental autoimmune encephalomyelitis (*J Clin Invest.* 2009; 119(12):3678-3691). Furthermore, IL-10 promotes survival of neurons and oligodendrocytes by protecting them from inflammation-induced damage. It has been shown that TNF-α plays an important reparative role in the demyelinating brain. Lack of TNF-α led to a reduction in the pool of proliferating OPCs and subsequent significant delay in remyelination in CPZ-mediated demyelinated brain (Arnett H A, et al. *Nat Neurosci.* 2001; 4(11):1116-1122).

DUOC-01 cells also overexpress proteases that can regulate remyelination through modification of the extracellular matrix. MMP9 activity is required to clear NG2 chondroitin sulfate proteoglycan deposition and overcome the negative impact of NG2 on oligodendrocyte maturation and remyelination (Larsen P H, et al. *J Neurosci.* 2003; 23(35):11127-11135). High expression of MMP12, which is required for proteolysis and matrix invasion by macrophages in mice, might facilitate the migration of DUOC-01 from the injection site in the CC to other regions of the brain that was observed using CFSE-labeled cells. MMPs also play a role in angiogenesis, in the release of growth factors sequestered by the extracellular matrix, and in processing of cell-cell recognition molecules that allow repair.

In certain embodiments, the DUOC-01 cell product includes cells that secrete IL-6, IL-10, or both. In certain embodiments, the concentration of IL-6 in DUOC-01 cell product is between about 300 to about 2600 pg/$10^6$ cells/mL. In certain embodiments, the concentration of IL-10 in DUOC-01 cell product is between about 20 to about 250 pg/$10^6$ cells/mL.

In certain embodiments, the DUOC-01 cell product includes cells that overexpress one or more of platelet-derived growth factor subunit A (PDGFA), KIT-ligand (KITLG, also known as stem cell factor [SCF]), insulin-like growth factor-1 (IGF1), triggering receptor expressed on myeloid cells 2 (TREM2), matrix metalloproteinase-9 (MMP9), and MMP12 transcripts. In certain embodiments, the expression of one or more of PDGFA, KITLG, IGF1, TREM2, MMP9, and MMP12 transcripts is at least 5 times higher compared to CB $CD14^+$ monocytes, e.g., at least 10 times higher, or at least 15 times higher, or at least 20 times higher, or at least 25 times higher, or at least 30 times higher, or at least 50 times higher, or at least 100 times higher, or even 1000 times higher.

In certain embodiments, the DUOC-01 cell product includes cells that have unique RNA expression profile relative to CB $CD14^+$ monocytes.

In certain embodiments, the DUOC-01 cell product excludes cells expressing CD3 (i.e., DUOC-01 cell product cells do not express CD3). In certain embodiments, no more than 1% of the cell population, e.g., or no more than 0.5%, or no more than 0.1%, or even 0% of the cell population, expresses CD3 marker.

In certain embodiments, the DUOC-01 cell product may be a partially human leukocyte antigen (HLA)-matched to the subject.

The compositions of the invention useful in the methods of the disclosure include one or more anti-inflammatory agents. As used herein, the term "anti-inflammatory agent" refers to a drug or substance that reduces inflammation (e.g., redness, swelling, and pain) in the body. Anti-inflammatory agents can be steroidal or non-steroidal. Non-steroidal anti-inflammatory agents include, but are not limited to, indomethacin, ibuprofen, or acetylsalicylic acid. The anti-inflammatory agent can be an anti-cytokine agent (e.g., a monoclonal or polyclonal antibody directed against a cytokine). The cytokines can be, for example, a tumor necrosis factor, an interleukin, or an interferon.

Steroidal anti-inflammatory agents include, but are not limited to, corticosteroids. In some embodiments, the anti-inflammatory agent is a corticosteroid, which includes, but is not limited to, cortisone, hydrocortisone, triamcinolone, dexamethasone, or beclomethasone. In certain embodiments, the anti-inflammatory agent is hydrocortisone ("HC").

In some embodiments, the DUOC-01 cell product and the anti-inflammatory agent are administered in combination, i.e. they are formulated together with a pharmaceutically acceptable carrier to create a composition suitable for administration to a subject in need thereof. The composition may be prepared and suitably stored in advance of administration, or the composition may be prepared immediately prior to administration. The composition may be prepared at any time in advance of administration. In non-limiting examples, the composition may be prepared 2 hours or 4 hour prior to administration.

In other embodiments, the DUOC-01 cell product and the anti-inflammatory agent are administered in conjunction with each other. In certain embodiments, they are administered concurrently, i.e. at the same time. In other embodiments, the anti-inflammatory agent is administered prior to or after administration of the DUOC-01 cell product. Suitable dosing levels for the DUOC-01 cell product and the anti-inflammatory agent for such administration can be determined by one of skill in the art.

The route of administration of the compositions of the disclosure may be selected by one of skill in the art based on the diseases treated and desired results. Thus, in one embodiment, the composition is administered via local tissue injection, intrathecally (e.g., an administration into the spinal canal, or into the subarachnoid space, or into space under the arachnoid membrane of the brain), or intracerebrally (e.g., an administration into the cerebrum). In certain embodiments, the composition is administered intrathecally, such as via an intrathecal injection. In certain embodiments, the composition is administered via local tissue injection, e.g., into a local area where a peripheral nerve has been damaged. For example, in certain embodiments, the local tissue injection may be into the tissue adjacent to the damaged nerve (e.g., prostate, diaphragm, extremities, bladder, bowel, etc.).

The compositions of the disclosure may be administered in a single dose. The compositions of the disclosure may also be administered in multiple doses (e.g., two, three, or more single doses per treatment) over a time period (e.g., minutes, hours, or even several days). In certain embodiments, the compositions of the disclosure may be administered over a time period in the range of about 1 second to about 3 minutes, e.g., over about 60 seconds to about 120 seconds, or over about 90 seconds to about 120 seconds, or over about 60 seconds to about 180 seconds, over about 90 seconds to about 180 seconds, or over about 1 seconds to about 15 seconds, or over about 5 seconds to about 15 seconds, or over about 1 seconds to about 30 seconds, or over about 5 seconds to about 30 seconds, or over about 15 seconds to about 60 seconds, or over about 15 seconds to about 90 seconds.

The DUOC-01 cell product may be present in the composition in a therapeutically effective concentration. In certain embodiments, the concentration of DUOC-01 cell product in the composition is about $1 \times 10^4$ to about $1 \times 10^8$ cells/dose of composition; e.g., about $1 \times 10^5$ to about $1 \times 10^8$ cells/dose, or about $1 \times 10^6$ to about $1 \times 10^8$ cells/dose, or about $1 \times 10^7$ to about $1 \times 10^8$ cells/dose, or about $1 \times 10^6$ to about $5 \times 10^7$ cells/dose, about $1 \times 10^5$ to about $1 \times 10^7$ cells/dose, or about $1 \times 10^6$ to about $1 \times 10^7$ cells/dose, or about $1 \times 10^6$ to about $5 \times 10^6$ cells/dose, or about $1 \times 10^6$ to about $5 \times 10^6$ cells/dose of composition. One of skill in the art will recognize that suitable volume of the dose may be selected based on the desired route of administration. For example, intrathecal administration may use dose volumes in the range of about 1 mL to about 10 mL; e.g., about 5 mL, or about 4 mL to about 6 mL, or about 3 mL to about 7 mL, or about 1 mL to about 5 mL, or about 5 mL to about 10 mL. For example, intracerebral administration or local tissue injection may use dose volumes in the range of about 0.5 mL to about 2 mL; e.g., about 1 mL, or about 0.5 mL to about 1.5 mL, or about 0.5 mL to about 1 mL, or about 1 mL to about 1.5 mL, or about 5 mL to about 10 mL.

In certain embodiments, the DUOC-01 cell product is present in the composition in the amount of about $1 \times 10^4$ to about $1 \times 10^8$ cells; e.g., about $1 \times 10^5$ to about $1 \times 10^8$, or about $1 \times 10^5$ to about $1 \times 10^7$ cells, or about $1 \times 10^5$ to about $1 \times 10^6$ cells, or about $1 \times 10^6$ to about $1 \times 10^8$ cells, or about $1 \times 10^6$ to about $1 \times 10^7$ cells, or about $1 \times 10^6$ to about $5 \times 10^6$ cells.

The anti-inflammatory agent may be present in the composition in a therapeutically effective concentration. In certain embodiments, the concentration of the anti-inflammatory agent in the composition is about 0.5 mg/mL to about 5 mg/mL. or any range falling within this range, for example about 1 mg/mL to about 4 mg/mL, or about 0.5 mg/mL to about 3 mg/mL, or about 3 mg/mL to about 5 mg/mL, or about 2 mg/mL to about 4 mg/mL. In some embodiments, the anti-inflammatory agent is present in the composition at a concentration of 0.5 mg/mL, or 1 mg/mL, or 2 mg/mL, or 3 mg/mL, or 4 mg/mL, or 5 mg/mL.

Any suitable pharmaceutically acceptable carrier may be used in the compositions of the disclosure. In certain embodiments, the pharmaceutically acceptable carrier is Ringer's lactate solution. In certain embodiments, the pharmaceutically acceptable carrier is Ringer's solution, Tyrode's solution, or a saline solution.

The compositions useful in the methods of the disclosure may be obtained by exposing the cord blood mononuclear cells in a first culture medium to one or more factors selected from: platelet-derived growth factor (PDGF), neurotrophin-3 (NT-3), vascular endothelial growth factor (VEGF), and triiodothyronine ($T_3$); and at least one of serum or plasma for a period of time sufficient to obtain DUOC-01 cell product. After isolating the DUOC-01 cell product, the DUOC-01 cell product may be dissolved in the pharmaceutically acceptable carrier to obtain the composition of the disclosure. In certain embodiments, an additional amount of PDGF, NT-3, VEGF, $T_3$, and serum after 7 days and after 17 days may be provided. In certain embodiments, an additional amount of PDGF, NT-3, and VEGF after 14 days may be provided.

In certain embodiments, the period of time sufficient to obtain DUOC-01 cell product is about 21 days. In certain embodiments, the period of time sufficient to obtain DUOC-01 cell product is about 17 days, or 18 days, or 19 days, or 20 days, or 22 days, or 23 days, or 24 days.

In certain embodiments, the PDGF is present in a concentration of about 1 to about 10 ng/mL. In certain embodiments, the NT-3 is present in a concentration of about 0.1 to about 5 ng/mL. In certain embodiments, the VEGF is present in a concentration of about 1 to about 50 ng/mL. In certain embodiments, $T_3$ is present in a concentration of about 10 to about 100 ng/mL.

In certain embodiments, exposing the cord blood mononuclear cells in a first culture medium is to PDGF, NT-3, VEGF, $T_3$, and serum.

Another aspect of the disclosure provides a kit comprising a composition comprising a DUOC-01 cell product and an anti-inflammatory agent as described herein in a pharmaceutically acceptable carrier; and a label or instructions for administration of the composition to treat a demyelinating condition. In certain embodiments of the disclosure, the kit is for treating multiple sclerosis in a subject. In certain embodiments of the disclosure, the kit is for treating leukodystrophies in a subject. In certain embodiments of the disclosure, the kit is for treating spinal cord injury in a subject.

Certain aspects of the disclosure are now explained further via the following non-limiting examples.

EXAMPLES

Materials and Methods

The materials and methods of the present disclosure are in accordance with those described in International Application No. PCT/US18/13606, which is incorporated by reference herein in its entirety.

Example 1: Safety of DUOC-01 Administration

Twenty children with inherited leukodystrophies have been treated with a single intrathecal dose of DUOC-01 as adjunctive therapy to HSCT after myeloablative chemotherapy with unrelated umbilical cord blood donors. Of these, 17 patients received DUOC-01 manufactured from the 20% fraction of the cord blood unit utilized for HSCT. In 14 of these patients, DUOC-01 was administered on days 28, in one on day 27, and in two on day 42. The other three patients received DUOC-01 manufactured from a different donor than their HSCT donor. The donors for HSCT and DUOC were 4/6 matches to each other and to the patient. In all three patients, DUOC-01 was administered on day +42 post-transplant (Table 1).

TABLE 1

Administration of DUOC
Administration of DUOC
# of patients treated on post transplant day

|  | +27/28 | +42 | Total Patients |
|---|---|---|---|
| # HSCT Donor | 15 | 2 | 17 |
| # 3$^{rd}$ Party Donor | 0 | 3 | 3 |
| Total Patients | 15 | 5 | 20 |

The median age of the 20 patients was 2.54 years (range 0.06-11.45 years). Their diagnoses included Krabbe disease (n=3), metachromatic leukodystrophy (n=7), Pelizaeus-Merzbacher disease (n=2), adrenoleukodystrophy [ALD] (n=2), Tay Sachs disease (n=1), Hunter Syndrome (n=1), Sanfilippo Syndrome, Type A (n=1), and Batten disease (n=3). The three patients receiving third party cord blood were 1.77, 4.68, and 11.45 years, respectively. Their diagnoses were ALD, Sanfilippo Type A, and Batten disease, respectively.

Yields of DUOC-01 post manufacturing were highly variable. The median cell dose of the 20 treated patients was $20.65 \times 10^5$ (range $0.2-155 \times 10^5$) DUOC-01 cells. The 3 patients receiving $3^{rd}$ party cells received 95, 45, and $155 \times 10^5$ DUOC-01 cells.

Two of the three patients receiving $3^{rd}$ party DUOC-01 experienced low grade fever and hypotension 2 and 6 hours after the intrathecal injection. The affected patients were the 11 year old with ALD and the 2 year old with Sanfilippo A. Both patients were on systemic steroids at the time of DUOC-01 administration due to treatment of engraftment syndrome and the patient with ALD was on replacement therapy because of adrenal insufficiency associated with ALD. Both patients had spontaneous resolution of symptoms within 18 hours. The patient with ALD required fluid, resuscitation, and additional steroid therapy for 12 hours. Each patient underwent a repeat lumbar puncture 24 hours after initial DUOC administration to assess CSF for cell count, protein and inflammatory cytokines. Of note, CSF was normal on the day of DUOC-01 administration. Repeat CSF in both patients showed a pleocytosis predominantly comprised of granulocytes presumed to be of HSCT origin. This was assumed because both patients were full chimeras with HSCT donor cells engrafted in studies of peripheral blood. Cytokines (IL-1 beta, IL-4, IL-5, and IL-10) were detected in the CSF and IL-6 and IL-8 were markedly elevated in the CSF of the second patient, but not in the peripheral blood. Cytokines were not measured in the CSF of the first patient. Sterility cultures were negative and protein and glucose were normal in the CSF in both patients.

After this event, the third party donor section of the protocol was put on hold while additional studies were pursued in the laboratory and in the clinic. Two patients were treated with DUOC-01 manufactured from their HSCT donor on day +42. Neither experienced a clinical reaction further supporting the hypothesis that the reaction in 2 of the 3 patients receiving third party donor cells were mediated by donor versus donor alloreactivity. A decision was made to supplement the intrathecal dose of DUOC-01 with hydrocortisone ("HO"), which has been used in combination with intrathecal chemotherapy in children and adults for decades. Effects of hydrocortisone were assessed on DUOC-01 final stability and also on its potency in the cuprizone model which assesses its ability to induce remyelination of demyelinated brain. The results of these experiments are shown below in Example 2.

Example 2: Hydrocortisone Does not Alter the Stability, Identity or Potency of DUOC-01 Cells With the plan to add hydrocortisone ("HO") to the DUOC-01 formulation for intrathecal injection, it was necessary to demonstrate that HC did not alter the stability, identity or potency of DUOC-01 cells.

HC on the stability and phenotype of DUOC-01 cells.

Figure 1:
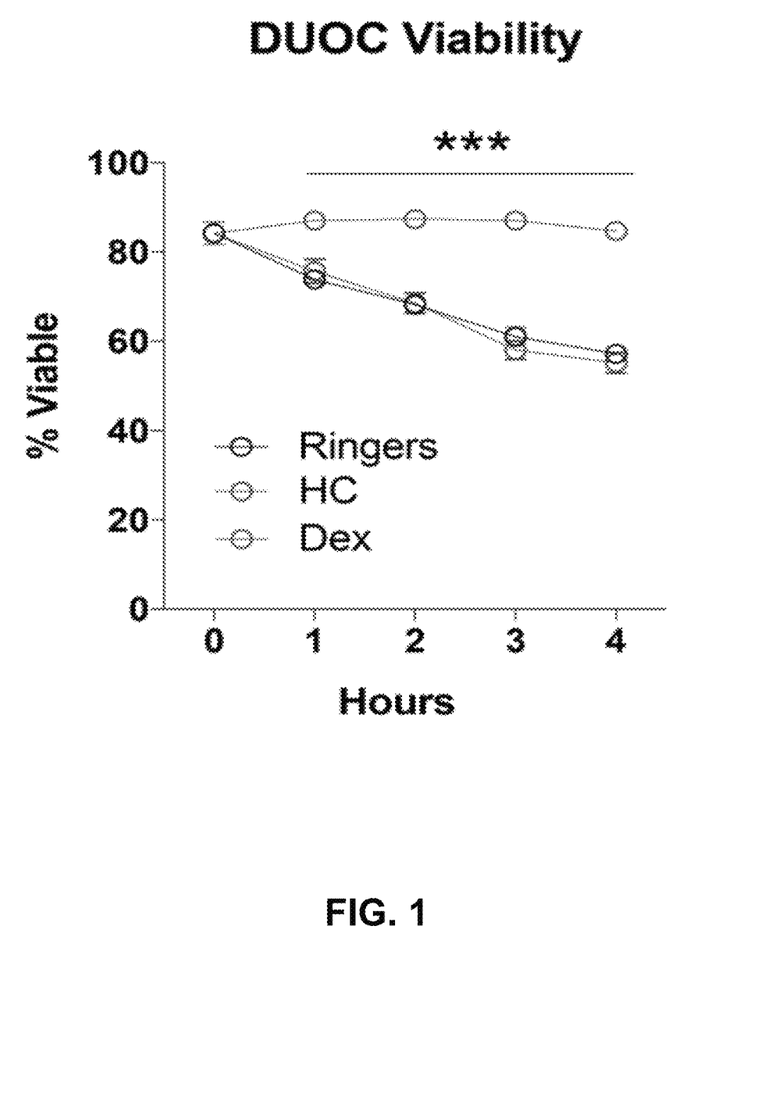
FIG. 1 illustrates that HC increases the viability of DUOC-01 cells over time. Viability was measured by AOPI using the Nexcelom Cellometer Auto 2000 (n=6 samples per time point; 2-way ANOVA p<0.001 for treatment factor; Tukey's post-hoc***>0.001).
Figure 2A:
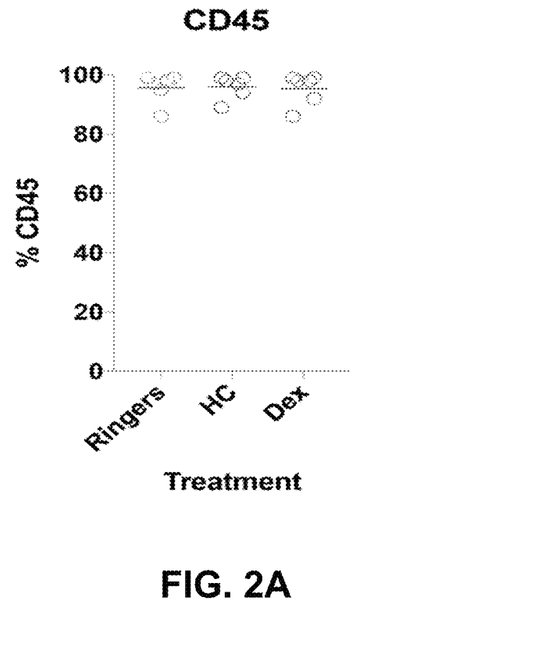
FIGS. 2A-2D illustrate that HC does not change the expression of common DUOC-01 cell surface markers. DUOC-01 cells were collected 4 hours after adding HC or dexamethasone (Dex). The expression of CD45 (FIG. 2A), CD11b (FIG. 2B), Trem2 (FIG. 2C), and CD14 (FIG. 2D) were analyzed by flow cytometry (n=6 per condition).
Figure 2B:
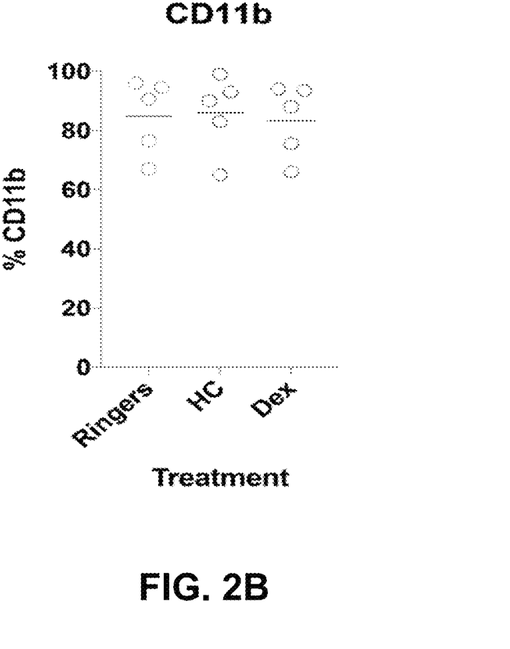
Figure 2C:
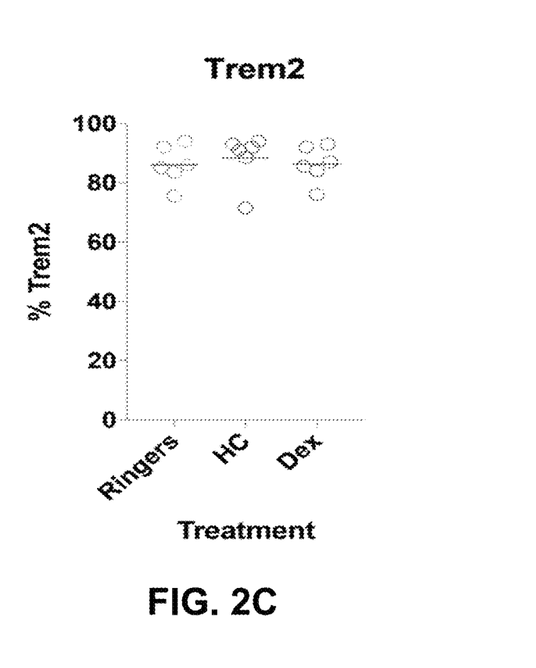
Figure 2D:
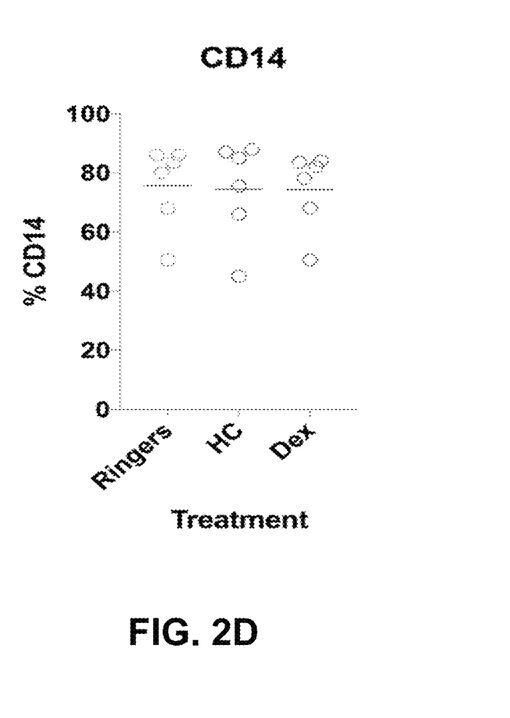

First, to test stability, day +21 DUOC-01 cells were harvested into ringers lactate and incubated with HC for up to 4 hours to determine whether there was any change in viability or stability. HC did not decrease viability or alter the phenotype of DUOC-01 cells in vitro; in fact, HC improved the viability DUOC-01 cells over time (FIG. 1). HC did not change the expression level of surface markers used for standard characterization of DUOC-01 cells (FIGS. 2A-2D).

DUOC-01 cells were cultured using standard procedures from cryopreserved and thawed cord blood units, then harvested on day 21 and re-suspended in Ringers. After initial count and viability, the cell suspension was divided into three conditions: (1) Ringer's solution, (2) 3 mg/ml HC, (3) 25 ng/ml Dex.

Based on previous stability studies, the cells were incubated for 4 hours at room temperature and characterized every hour for 4 hours. The viability of DUOC-01 cells over time was consistently greater with cells incubated with HC compared to DUOC-01 cells incubated with dexamethasone or Ringer's solution (FIG. 1). All conditions throughout the time course did not change the basic phenotype (i.e., surface expression of CD45, CD14, TREM2, and CD11b; FIGS. 2A-2D). Total viable cell counts are listed in Table 2.

TABLE 2

Treating DUOC-01 cells with HC or Dex did not change the total viable cells harvested

| Average of six experiments | Averaged total viable cell numbers | | | |
|---|---|---|---|---|
| | 1 hr | 2 hr | 3 hr | 4 hr |
| untreated ave. | 1,102,708 | 1,014,792 | 968,750 | 775,625 |
| HC (3 mg/ml) ave. | 959,688 | 821,667 | 910,604 | 742,000 |
| Dexamethazone (25 ng/ml) ave. | 923,563 | 813,750 | 821,250 | 706,875 |

Effects of HC on the ability of DUOC-01 cells to promote remyelination.

To test whether HC would impact the ability of DUOC-01 cells to promote remyelination, a standard mouse model of demyelination showed that DUOC-01 cells exposed to HC promoted remyelination to the same extent as standard DUOC-01 cells.

DUOC-01 cells were cultured via standard procedures from frozen cord blood units in the GMP facility and harvested on day 21. After initial count and viability, the cell suspension was split into two conditions at a concentration of 20,000 cells/µl: (1) Ringers, and (2) Ringers +3 mg/ml HC.

Figure 3:
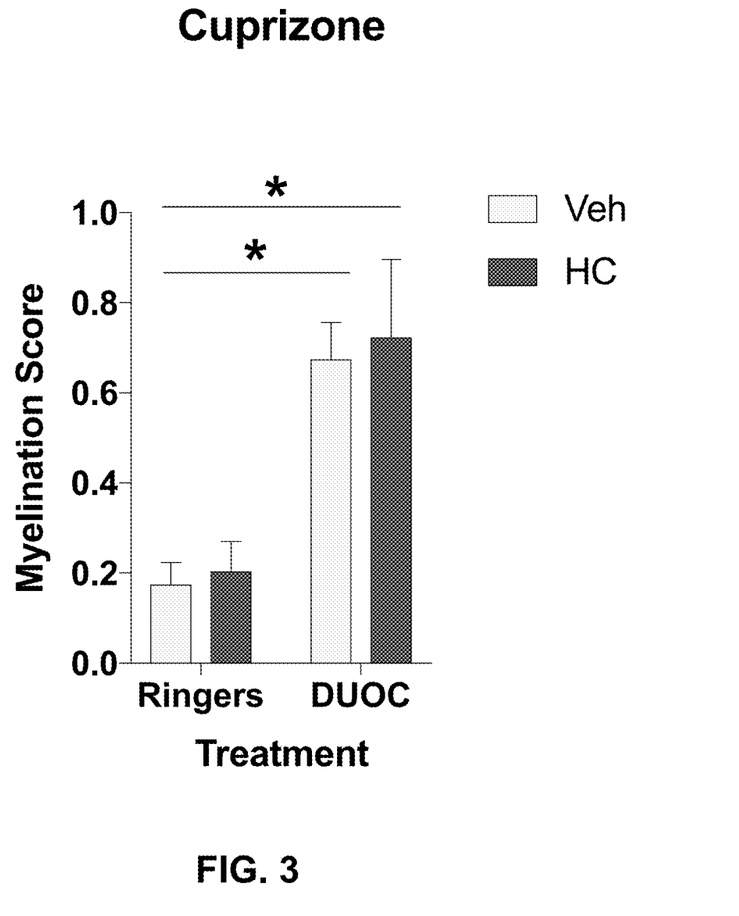
FIG. 3 illustrates that HC does not inhibit DUOC-01 cells from promoting remyelination. Myelination score based on LFB-PAS staining of mice one week after treatment of CPZ-treated mice with, Ringer's, Ringers+HC, DUOC-01 cells, or DUOC-01 cells exposed to HC ($1\times10^5$ cell injected). DUOC-01 treatment for 1-week increased myelination in the corpus callosum area compared to Ringer's injected controls. Two independent, blinded readers scored coded LFB-PAS stained sections at the mid-line corpus callosum area, between zero and 3. Data are presented as mean ±SEM (ANOVA for cells P<0.001; n=9-16 mice per group, *P<0.05, Tukey's post-hoc test; pooled 2 independent experiments).

Based on previous stability studies, the cells were incubated in HC for 2 hours at room temperature prior to injections. To determine if HC would affect the ability of DUOC-01 cells to promote remyelination, Ringer's solution or DUOC-01 cells was injected into the corpus callosum of NSG mice treated with cuprizone, as previously described (Saha et al. JCI Insight 2016). One week following treatment, brains were harvested and analysis of myelination by LFB-PAS staining was conducted. HC did not inhibit the ability of DUOC-01 cells to promote remyelination (FIG. 3).

Example 3: Safety of Administration of DUOC-01 in Combination with Hydrocortisone Twenty seven (27) patients were treated with intrathecal doses of DUOC-01. The last 8 patients received DUOC in hydrocortisone. Of these, five patients received a formulation with hydrocortisone manufactured from a different cord blood unit than the donor used for their transplant. Seven of these patients received DUOC-01 within 2 months of their hematopoietic stem cell transplant (HSCT). One, the most recent, under eIN D, received their transplant 6 years post HSCT. All patients tolerated the DUOC therapy from a third party donor, manufactured from a whole cord blood unit, without toxicity.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A pharmaceutical composition comprising therapeutically effective amounts of a DUOC-01 cell product and an anti-inflammatory agent, in a pharmaceutically acceptable carrier, wherein the anti-inflammatory agent is cortisone, hydrocortisone, triamcinolone dexamethasone or beclomethasone.

2. The pharmaceutical composition of claim 1, wherein the anti-inflammatory agent improves the viability of the DUOC-01 cell product.

3. The pharmaceutical composition of claim 1, wherein the anti-inflammatory agent is hydrocortisone.

4. The pharmaceutical composition of claim 1, wherein the DUOC-01 cell product comprises an amount of about $1 \times 10^4$ to about $1 \times 10^8$ cells/dose.

5. A method of treating a demyelinating condition in a subject in need thereof, the method comprising: administering to the subject a pharmaceutical composition comprising therapeutically effective amounts of a DUOC-01 cell product and an anti-agent is cortisone, hydrocortisone, triamcinolone, dexamethasone, or beclomethasone a therapeutically effective amount of the composition of claim 1.

6. The method of claim 5, wherein the DUOC-01 cell product comprises cells derived from cord blood mononuclear cells, wherein such cells express one or more of CD45, CD11b, CD14, CD16, CD206, CD163, Ibal, HLA-DR, TREM 2, and iNOS macrophage or microglia markers.

7. The method of claim 5, wherein the demyelinating condition is a leukodystrophy.

8. The method of claim 5, wherein the demyelinating condition is Krabbe disease, metachromatic leukodystrophy, Pelizaeus-Merzbacher disease, adrenoleukodystrophy (ALD), Tay Sachs disease, Hunter Syndrome, Sanfilippo Syndrome, Type A, or Batten disease.

9. The method of claim 5, wherein the demyelinating condition is multiple sclerosis.

10. The method of claim 5, wherein the demyelinating condition is spinal cord injury, peripheral nerve damage, Parkinson's disease, amyotrophic lateral sclerosis (ALS), or Alzheimer's disease.

11. The method of claim 5, wherein the composition is administered via local tissue injection or intrathecally.

12. The method of claim 5, wherein the composition is administered in a single dose or in multiple doses.

13. The method of claim 5 wherein the amount of composition administered is sufficient to provide the DUOC-01 cell product in an amount of about $1 \times 10^5$ to about $1 \times 10^7$ cells or about $1 \times 10^6$ to about $5 \times 10^6$ cells.

14. A kit comprising: therapeutically effective amounts of (i) a composition comprising a DUOC-01 cell product and (ii) an anti-inflammatory agent in a pharmaceutically acceptable carrier, wherein the anti-inflammatory agent is cortisone, hydrocortisone, triamcinolone dexamethasone or beclomethasone, and a label or instructions or administration of the components of the kit to treat a demyelinating condition.

15. A method of treating a demyelinating condition in a subject in need thereof, the method comprising administering to the subject (i) a therapeutically effective amount of a DUOC-01 cell product in conjunction with (ii) a therapeutically effective amount of an anti-inflammatory agent, wherein the anti-inflammatory agent is cortisone, hydrocortisone, triamcinolone dexamethasone or beclomethasone.

16. The method of claim 15, wherein the DUOC-01 cell product and the anti-inflammatory agent are administered concurrently.

17. The method of claim 15, wherein the anti-inflammatory agent is administered prior to the administration of the DUOC-01 cell product.

18. The method of claim 15, wherein the anti-inflammatory agent is administered after the administration of the DUOC-01 cell product.

* * * * *